United States Patent
Yokoyama et al.

(10) Patent No.: US 7,202,580 B2
(45) Date of Patent: Apr. 10, 2007

(54) PERMANENT MAGNET TYPE MOTOR AND X-RAY COMPUTED TOMOGRAPHY APPARATUS

(75) Inventors: Akiyuki Yokoyama, Yokohama (JP); Masahiro Kuroda, Yokohama (JP); Tadahiro Nakayama, Yokohama (JP); Shinichi Kominato, Tokyo (JP); Tomokazu Harada, Otawara (JP); Yoshinori Saito, Yaita (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 10/845,114

(22) Filed: May 14, 2004

(65) Prior Publication Data

US 2005/0116558 A1 Jun. 2, 2005

(30) Foreign Application Priority Data

May 16, 2003 (JP) .............................. 2003-139073

(51) Int. Cl.
*H02K 1/27* (2006.01)
*H02K 21/14* (2006.01)
*A61B 6/00* (2006.01)

(52) U.S. Cl. .................................................. 310/68 B
(58) Field of Classification Search ...................... None
See application file for complete search history.

(56) References Cited

U.S. PATENT DOCUMENTS

| | | | | |
|---|---|---|---|---|
| 4,970,423 | A * | 11/1990 | Tamae et al. ................ | 310/162 |
| 6,553,091 | B2 * | 4/2003 | Takanashi et al. ............ | 378/15 |
| 6,590,953 | B2 * | 7/2003 | Suzuki et al. ................ | 378/15 |
| 6,700,947 | B2 * | 3/2004 | Oshima et al. ............... | 378/15 |
| 6,713,981 | B2 * | 3/2004 | Nakajima .................... | 318/491 |
| 6,819,737 | B2 * | 11/2004 | Suzuki et al. ................ | 378/15 |

FOREIGN PATENT DOCUMENTS

| JP | 63-63083 | 4/1988 |
|---|---|---|
| JP | 2-30284 | 2/1990 |
| JP | 2-114373 | 9/1990 |

(Continued)

OTHER PUBLICATIONS

JPO English Abstract, JP2002-010608, Nakayama, Jan. 11, 2002.*

(Continued)

*Primary Examiner*—Burton Mullins
(74) *Attorney, Agent, or Firm*—Oblon, Spivak, McClelland, Maier & Neustadt, P.C.

(57) ABSTRACT

A permanent magnet type motor comprising a rotor main body rotatably supported with respect to a stationary member, a rotor which is provided on an outer periphery face of the rotor main body and which is arranged such that S poles and N poles of a plurality of permanent magnets are provided alternately, a stator composed of a stator core arranged at the outer periphery side or inner periphery side of the rotor, the stator core having winding storage sections, and stator windings stored in the winding storage sections, a sensor fixed to the stationary member so as to be proximal to the permanent magnets, the sensor detecting a position of the permanent magnets, a detection target member having a detector for detecting a magnetic resistance change portion formed on the rotor main body, and a rotational position detecting magnetic sensor arranged at the stationary member.

13 Claims, 8 Drawing Sheets

FOREIGN PATENT DOCUMENTS

| | | |
|---|---|---|
| JP | 5-236718 | 9/1993 |
| JP | 6-98882 | 4/1994 |
| JP | 6-98884 | 4/1994 |
| JP | 10-70875 | 3/1998 |
| JP | 2001-298932 | 10/2001 |
| JP | 2002-598 | 1/2002 |
| JP | 2002-10608 | 1/2002 |
| JP | 2002-78703 | 3/2002 |
| JP | 2002-340614 | 11/2002 |
| JP | 2003-70193 | 3/2003 |

OTHER PUBLICATIONS

JPO English Abstract, JP2002-000598, Yokayama, Jan. 8, 2002.*

* cited by examiner

US 7,202,580 B2

PERMANENT MAGNET TYPE MOTOR AND X-RAY COMPUTED TOMOGRAPHY APPARATUS

CROSS-REFERENCE TO RELATED APPLICATIONS

This application is based upon and claims the benefit of priority from prior Japanese Patent Application No. 2003-139073, filed May 16, 2003, the entire contents of which are incorporated herein by reference.

BACKGROUND OF THE INVENTION

1. Field of the Invention

The present invention relates to a permanent magnet type motor and an X-ray computed tomography (hereinafter, referred to as X-ray CT) apparatus.

2. Description of the Related Art

Conventionally, it has been well known that an example of X-ray CT apparatus is configure as shown in FIG. 11 which is a partial sectional view showing essential portions thereof. The conventional X-ray CT apparatus comprises: a stationary tubular frame 51 having a small diameter portion and a large diameter portion to form a substantially L shaped cross section with respect to a tube axis O; a bearing 52 arranged at the small diameter portion of the frame 51; a rotational tubular frame 53 having a small diameter portion rotationally connected to a movable side of the bearing 52 and a larger diameter portion to form a substantially L shaped cross section with respect to the tube axis O; a ring shaped rotor 54 fixed at the large diameter portion of the rotational tubular frame 53; a stator 57 having a stationary iron core 55 fixed at the inner periphery side of the larger diameter portion of the frame 51 to face the rotor 54 via a predetermined gap therebetween and a stator winding 56 wound on the core 55; and a slip ring 58 fixed on the inner side of the large diameter portion of the rotational tubular frame 53 and adopted to supply power to an X-ray tube (not shown) fixed on the rotational tubular frame 53.

In addition, a gear 59 made of a magnetic material is fixed at an end part of the large diameter portion of the rotational tubular frame 53. A magnetic sensor 60 is fixed on the end of the stationary tubular frame 51 to be proximal to the gear 59. With these magnetic sensor 60 and gear 59, a rotational position of the rotor 54, i.e., a rotational position of the X-ray tube is detected. In this case, when a tooth of the gear 59 or a protrusive portion thereof is opposed to the magnetic sensor 60, the magnetic flux density crossing the sensor 60 increases and the resistance value thereof increases. In contrast, when a tooth groove or a recess portion of the gear 59 is opposed to the magnetic sensor 60, the magnetic flux density decreases, and the resistance value decreases. Thus, the rotational position of the X-ray tube is detected.

Further, a plurality of pairs of permanent magnets 61 each configuring a magnetic pole are fixed at the outer periphery portions of the rotor 54. A Hall effect device or a Hall effect IC utilizing a Hall effect, although not shown, is disposed on the stationary tubular frame 51 by means of a support member (not shown) in proximity to the side surface of the permanent magnets 61. By this Hall effect IC, a magnetic pole position of the permanent magnet 61 can be detected.

The rotational tubular frame 53 supports an X-ray detector for detecting an X-ray emitted from the X-ray tube and transmitted through a detection target, in addition to the X-ray tube. In addition, is mounted on the stationary tubular frame 51 a computer section which reconstructs tomographic image data of the detection target based on an output of the X-ray detector and a rotational position of the X-ray tube on the rotational tubular frame 53. A signal transmission system storage section 62 is designed so as to transmit X-ray data detected by the X-ray detector to the computer section on the stationary tubular frame 51 which is included in an X-ray related device storage section 63 via an optical communication line. In FIG. 11, the X-ray related device storage section 63 comprises the above-described X-ray rube, X-ray detector, computer section, and a power source for the X-ray tube. In addition, a substantially tapered internal sheath cover 26 is arranged at the inner periphery side of the rotational tubular frame 53.

In the above-described conventional X-ray CT apparatus, the rotor 54 for rotating the rotational frame 53 is disposed and fixed at the outer surface side of the large diameter portion of the rotational frame 53 which is distant from the bearing 52 or the center axis O. In addition, the stator 57 is positioned at the outer periphery side of the rotor 54 and is fixed at the inner periphery surface of the stationary tubular frame 51 via a predetermined gap from the rotor 54. Further, the slip ring 58, positioned on the large diameter portion of the rotational tubular frame 53 and adopted to supply power to the X-ray tube, is disposed and fixed at the inner periphery side of the rotational frame 53 at a position at which the rotor 54 is disposed. Thus, there has been a problem that the whole X-ray CT apparatus is large sized.

Moreover, the fact that the whole X-ray CT apparatus is large sized causes a problem with respect to the cost reduction of the X-ray CT apparatus.

On the other hand, as an example of the electric motor used for the conventional X-ray CT apparatus, an electric motor provided with a magnet type encoder is used. FIG. 12 shows a part of this type of motor having a magnetic gear 59 which is composed as a piece other than a motor section 64. The gear 59 is provided as a detection body of the magnet type encoder. The gear 59 is made of a thick magnetic material by means of cutting processing.

In addition, a resolver (not shown) is mainly used as a rotation position detector of a large diameter motor of hollow shaft type without providing a motor shaft, such as that shown in FIG. 11.

Like a motor, the resolver is composed of a stator and a rotor. Two pairs of windings shifted by 90 degrees each other are disposed at the stator and rotor, respectively. When the stator is energized as a primary side, an output voltage signal fluctuates in response to a rotational position of the rotor acting as a secondary part. A rotational position of the rotor is detected by means of this output voltage signal.

In this way, a detection target of the magnet type encoder is provided other than the electric motor body, and thus, has a defect that the target requires a mount space and parts and assembly cost.

Further, in the large diameter motor of hollow shaft type, a resolver must be used. The resolver enables detection of an absolute position and has high precision. However, the resolver is high in cost from a structural aspect.

BRIEF SUMMARY OF THE INVENTION

A permanent magnet type motor according to one aspect of the present invention comprises: a rotor main body rotatably supported with respect to a stationary member; a rotor provided on an outer periphery of the rotor main body and having a plurality of permanent magnets with N poles and S poles arranged alternately; a stator composed of a stator core arranged at the outer periphery side or inner periphery side of the rotor and having a stator winding storage portion, and a stator winding stored in the stator winding storage portion; a sensor fixed to the stationary member so as to be proximal to the permanent magnets for detecting a position of the permanent magnets; a detection target portion having a magnetic resistance change portion formed on the rotor main body; and a magnetic sensor arranged at the stationary member so as to be opposed to the detection target portion, the magnetic sensor detecting a rotational position of the rotor from a magnetic change relevant to the detection target portion.

An X-ray computed tomography apparatus according to another aspect of the present invention comprises: a stationary tubular frame having a cross section formed in a substantially tapered shape with respect to a tube axis; a bearing arranged at a small diameter side of the stationary tubular frame; a rotational tubular frame which is coupled to a movable side of the bearing at one end side thereof and which has a cross section formed in a substantially tapered shape with respect to the tube axis; an X-ray tube mounted on the rotational tubular frame; an X-ray detector which detects an X-ray emitted from the X-ray tube and transmitted through a target to be inspected; a rotational position detecting device which detects a rotational position of the X-ray tube by rotation of the rotational tubular frame; a computer section which reconstructs tomographic image data on the detection body based on an output of the X-ray detector and the rotational position of the X-ray tube obtained by the rotational position detecting device; a ring shaped rotor having a permanent magnet disposed and fixed at a link portion between the bearing and the rotational tubular frame, the permanent magnet being adopted to rotate the rotational tubular frame and having a plurality of magnetic poles on an outer periphery side of the ring shaped rotor; a stator which faces to an outer periphery of the rotor and which is fixed at an inner periphery of the stationary tubular frame via a predetermined gap from the rotor; a magnetic pole position detecting device which detects a magnetic pole position of the rotor; and a slip ring mounted on a large diameter side of the rotational tubular frame from a position where the rotor is disposed to supply electric power to the X-ray tube.

DETAILED DESCRIPTION OF THE INVENTION

Figure 1:
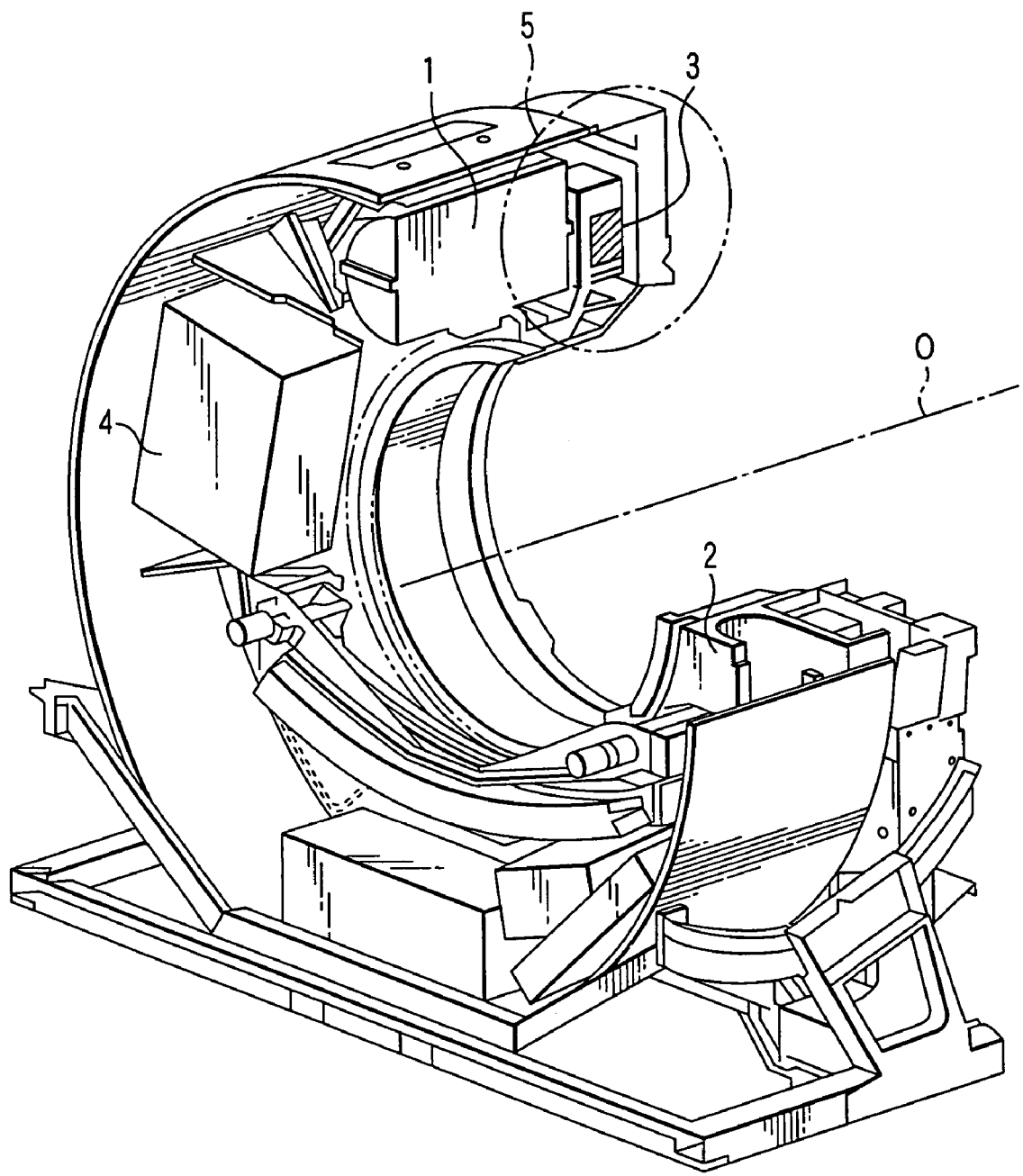
FIG. 1 is a perspective view showing a general configuration of an X-ray CT apparatus according to one embodiment of the present invention.

Hereinafter, a description will be given with respect to one embodiment of the present invention. First, a mechanism of an embodiment of an X-ray CT apparatus will be described with reference to FIGS. 1 and 2. FIG. 1 shows a part of the main configuration of the X-ray CT apparatus. That is, the figure shows an X-ray tube 1, an X-ray detector 2, a permanent magnet type motor 3, and a control device including an R-D converter, a motor control circuit, an image processing device.

Figure 2:
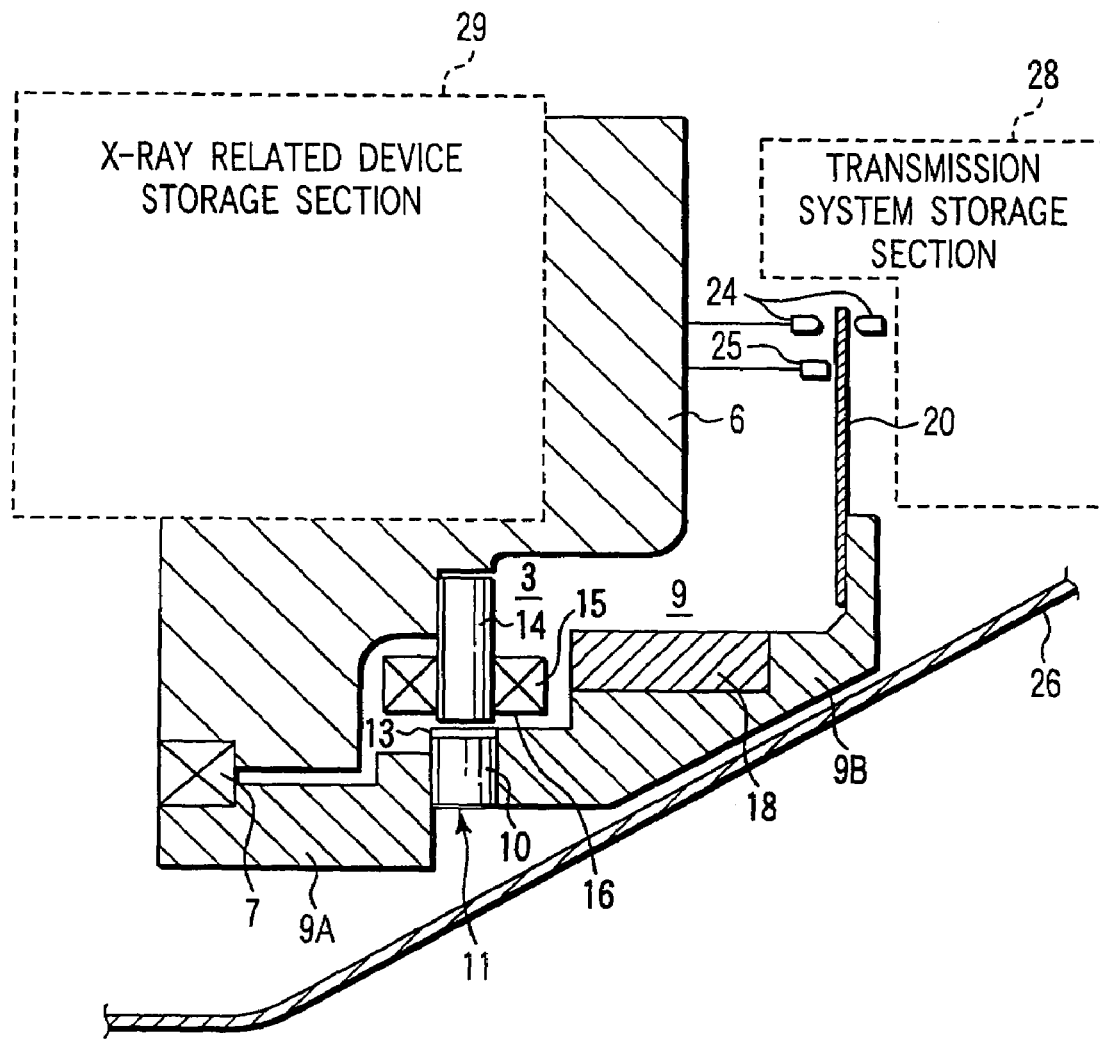
FIG. 2 is a schematic sectional view illustrating a configuration of the X-ray CT apparatus according to the one embodiment of the present invention.

FIG. 2 is a sectional view showing an enlarged portion enclosed in a two-dotted chain line circle 5 shown in FIG. 1. FIG. 2 shows a configuration comprising a stationary tubular frame 6 having a cross section formed in a substantially tapered shape with respect to a tube axis O; a bearing 7 arranged at an end of a small diameter portion of the stationary tubular frame 6; a cylindrical bearing sided rotational tubular frame 9A disposed and fixed at the inner periphery of the movable part of the bearing 7; and a substantial funnel shaped rotor sided rotational tubular frame 9B having one end part fixed in abutment with a side face of a rotor core 10 of a motor by means of a mount member (not shown). The frames 9A and 9B and the rotor core 10 are fixed together to form a rotational tubular frame 9. The intermediate part of the frame 9A between the bearing 7 and the rotor core 10 is used as a link member for linking the bearing 7 and the core 10.

At the rotor sided rotational tubular frame 9B, the X-ray tube 1 and the X-ray detector 2 shown in FIG. 1 are disposed and fixed so as to be opposed via a rotary axis O. The X-ray tube 1 and the X-ray detector 2 are mounted on the frame 9B so as to rotate along the periphery of a detection target (not shown) supported along the rotary axis O at the same time when the rotational tubular frame 9 rotates. The X-ray detector 2 detects the X-ray emitted from the X-ray tube 1 and transmitted through the detection target.

The X-ray CT apparatus further comprises a computer section (not shown) which reconstructs tomographic image data on the target to be inspected based on a rotational position of the X-ray tube 1 by an output of the X-ray detector 2 when the rotational tubular frame 9 rotates; and the permanent magnet type motor 3 composed of a rotor 11 and a stator 16, the rotor 11 being adopted to rotate the rotational tubular frame 9 composed of the frames 9A and 9B.

The rotor 11 includes the ring shaped rotor core 10 and a plurality of permanent magnets 13 mounted on the core 10. The plurality of permanent magnets 13 configuring plural pairs of magnetic poles N, S are disposed and fixedly mounted alternately on the outer periphery face of the rotor core 10.

The stator 16 is composed of: a ring shaped stator core 14 which is positioned near the outer periphery side of the rotor 11 and which is disposed on the stationary tubular frame 6 via a predetermined gap from the rotor 11; and a stator winding 15 wound and stored in a slot (not shown) of this stator ring core 14. This stator 16 is fixed to the inner periphery face of the stationary tubular frame 6 by means of a mount member (not shown).

Moreover, a slip ring 18 is mounted at the outer side of the rotational tubular frame 9B which is the large diameter part side opposite to the position at which the rotor 11 is disposed, and the slip ring 18 is provided to supply power to the X-ray tube 1.

Figure 9:
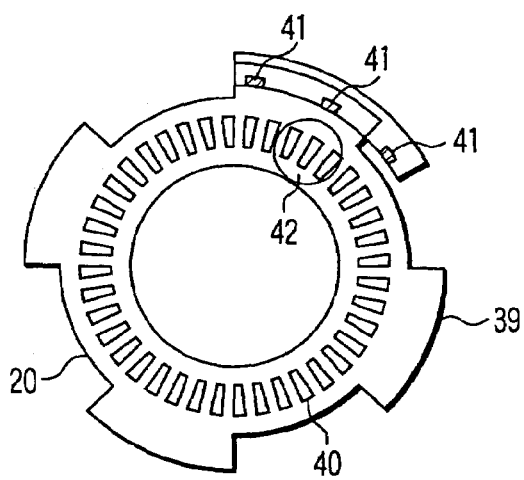
FIG. 9 is a schematic view of a forth embodiment motor with a slit plate according to the present invention.

Further, at the end side surface of the rotational tubular frame 9B, a disk shaped detection body 20 is directly fixed or mounted by means of a mount member (not shown). In the detection body 20, for example, as shown in FIG. 9, irregular portions including portions at which grooves are formed with equal intervals and portions existing between grooves configuring magnetic pole position detecting portions 39 are formed at the substantial disk shaped outer periphery portion of the body 20. Further, a plurality of slits 40 are periodically formed at the inner part of the body 20. The irregular portions configuring the magnetic pole position detecting portions 39 are formed at positions synchronizing with the permanent magnets 13 fixedly mounted on the outer periphery face of the rotor 11.

An optical sensor (of a transparent type or a reflection type) 41 for detecting the magnetic pole positions is fixed to the stationary tubular frame 6 so as to be proximal to the magnetic pole position detecting portions 39 of the detection body 20. In the case of FIG. 2, the optical sensor 24 acting as the sensor 41 is shown. Further, a magnetic sensor (MR sensor) 42 is disposed so as to be proximal to the slits 40 of the detection body 20, and the magnetic sensor 42 is fixed to the stationary tubular frame 6. In the case of FIG. 2, the magnetic sensor 25 acting as the sensor 42 is shown.

Here, the magnetic sensor 42 is composed of one set of two semiconductor magnetic-resistance elements and one magnet. This semiconductor magnetic-resistance element is referred to as an element for converting magneto-electricity so that a resistance value thereof increases in proportion to the strength of a magnetic field. An output of the magnetic sensor 42 causes the detection body 20 to act on the magnetic flux generated from the permanent magnet 13 mounted on the rear of the element, whereby a rotational position of the X-ray tube 1 is recognized from a voltage signal having two waveforms "sine" and "cosine" for outputting a voltage signal according to a resistance change of the magnetic resistance element or a magnetic sensing section.

In addition to the above-described configurations, an inside sheath cover 26, a transmission system storage section 28, an X-ray related device storage section 29 are provided.

According to the above-described X-ray CT apparatus, the rotor 11 of the permanent magnet type motor is connected to the rotational side of the bearing 7 via the link portion of the rotational tubular frame 9A, and thus, the whole system can be made compact. Concurrently, cost reduction can be achieved. Further, the motor is downsized in diameter, and thus, an inertial moment ($GD^2$) decreases. Furthermore, the motor weight is not almost changed, but the motor capacity or volume can be reduced. In addition, the inertial moment decreases, and thus, there is an advantage relevant to rigidity and strength aspect of the rotational tubular frames 9A, 9B, and a structure of the rotational tubular frames 9A, 9B can be easily reduced in weight. Moreover, the weight is small at the large diameter side of the rotational tubular frame 9A, and the detection body 20 having a small inertial moment is disposed. Since the motor which is large in weight is disposed at the small diameter side of the rotational tubular frame 9 close to the rotary axis O thereof, a structure of the rotational tubular frame 9 can cause easily to reduce the weight of the frame 9.

Figure 11:
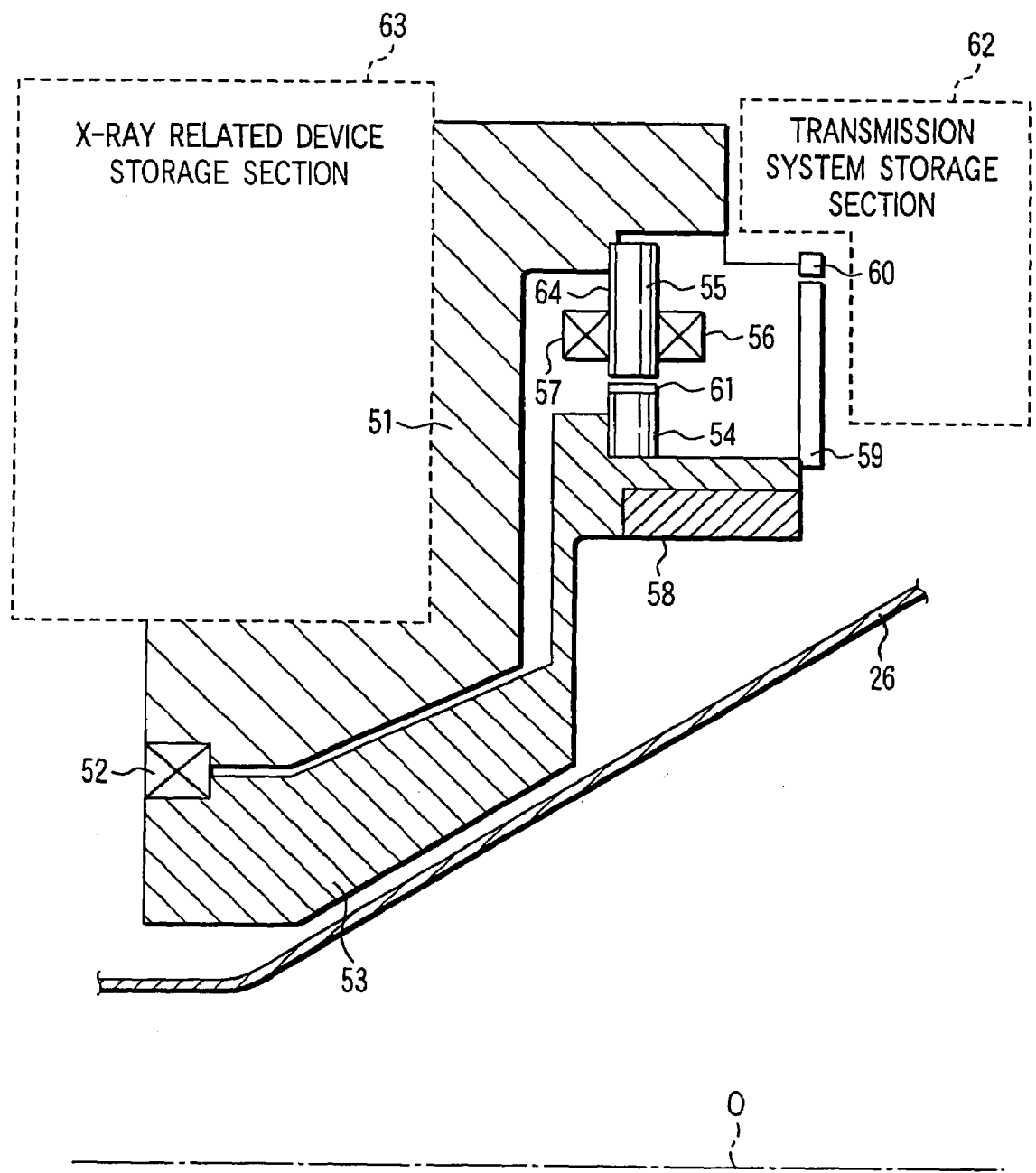
FIG. 11 is a view illustrating a configuration of a conventional X-ray CT apparatus.

The optical sensor 41 (or sensor 24 in FIG. 2) is arranged in proximity relevant to the irregular portions which configure the magnetic pole position detecting portion 39 provided on the detection body 20. In this manner, a magnetic pole position detecting device for detecting a magnetic pole position of the permanent magnet 13 is configured, and further, the magnetic sensor 42 (or sensor 25 in FIG. 2) is arranged in proximity to the plurality of slits 40 provided on the detection body 20. In this manner, a rotational position detecting device for detecting a rotational position of the rotor 11, i.e., X-ray tube 1 is configured, and thus, external dimensions of the motor 3 can be halved, for example, as compared with the conventional X-ray CT apparatus arranged respectively at different positions such as those shown in FIGS. 11 and 12. Further, by using the detection body 20, the whole weight decreases, the inertial moment decreases, and concurrently, the capacity or volume of the motor 3 can be reduced.

Further, as shown in FIG. 2, a motor rotating portion of the motor 3 and a sensor portion at the body 20 (magnetic pole position detection and rotational position detection) can be separated from each other. Thus, the detection body 20 can be placed at a position at which sensor adjustment is easy. In addition, by using the detection body 20, light is used for magnetic pole position detection, and a magnet is used for rotational position detection, and thus, interference in detecting both of these detection objects can be prevented.

Figure 3B:
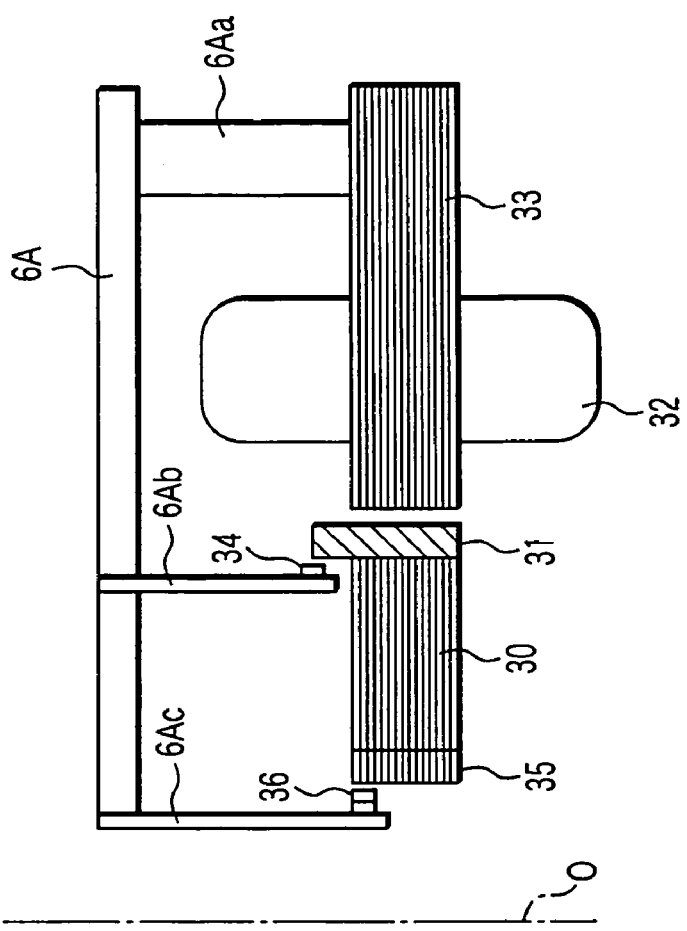
FIGS. 3A and 3B are sectional views in a radial direction and an axial direction, respectively, for illustrating a configuration of a permanent magnet motor according to a first embodiment of the present invention.
Figure 3A:
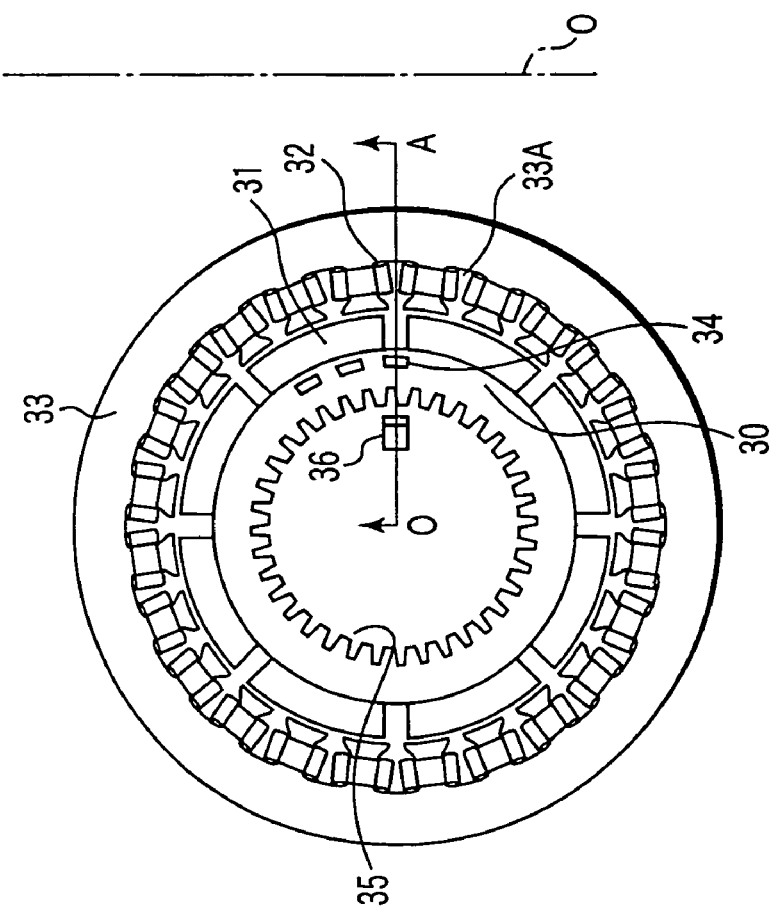

Now, some embodiments of a permanent magnet type motor according to the present invention other than that shown in FIG. 2 will be described with reference to FIGS. 3A to 10B. FIG. 3A shows a motor layout view and FIG. 3B shows a sectional view taken along the line O-A of FIG. 3A and seen in a direction indicated by the arrows, the views each illustrating a first embodiment of the permanent magnet type motor according to the present invention.

This configuration comprises a ring shaped rotor main body or a rotor yoke 30 rotatably supported by a bearing which is fixed at a stationary frame 6A via a link member (not shown); a plurality of permanent magnets 31 provided on the outer periphery of the rotor main body 30, the magnets 31 having alternately arranged S poles and N poles so that one end part protrudes in an axial direction from the surface of the rotor main body 30, and that the S and N poles are arranged so as to be periodic (equal in interval) in the circular direction; a stator core 33 which is fixed on the stationary frame 6A via a support member 6Aa and is formed in a ring shape in cross section, the stator core 33 having a plurality of slots 33A for storing a plurality of stator windings or stator coils 32 of plural phases; a sensor (Hall effect device or a Hall effect IC 34 fixed on the fixing member 6Ab so as to be proximal to a part of the inner periphery surface of the permanent magnet 31, the sensor 34 detecting a magnetic pole position of the permanent magnets 31; a detection target portion 35 having a gear-like magnetic-resistance change portion formed on the inner periphery face of the rotor main body 30; and a magnetic sensor or an MR sensor 36 mounted on the support member 6Ac coupled with the stationary frame 6A so as to be positioned opposite to the gear-like detection target portion 35, the magnetic sensor 36 detecting a rotational position of the rotor main body 30 from a magnetic change relevant to the lands and grooves of the detection target portion 35.

The magnetic-resistance change portion of the detection target portion 35 is formed on the inner periphery face of the rotor main body 30, and is an irregular portion consisting of a portion at which grooves are formed with equal intervals and land portions between these grooves arranged periodically in a rotary axis direction. The rotor main body 30 can be formed by laminating integrally a plurality of rotor body thin plate each of which is fabricated by pressing a thin iron plate or a silicon steel plate.

In such a configuration, the magnetic sensor 36 is composed of a semiconductor magnetic-resistance element acting as a magnetic sensing portion and a magnet. The magnetic sensor 36 causes a detection target portion 35 to act on the magnetic flux generated from the magnet mounted rearwardly of the semiconductor magnetic-resistance element 36, and the amount of the magnetic flux is changed, thereby outputting a voltage signal according to a resistance change of the magnetic-resistance element and recognizing a rotational position. With respect to the mount position of the magnetic sensor 36, a predetermined gap portion is provided to be opposed relevant to the land-groove irregular portion on the inner periphery face of the rotor main body 30, and the sensor 36 is mounted on the stationary member 6Ac.

Figure 12:
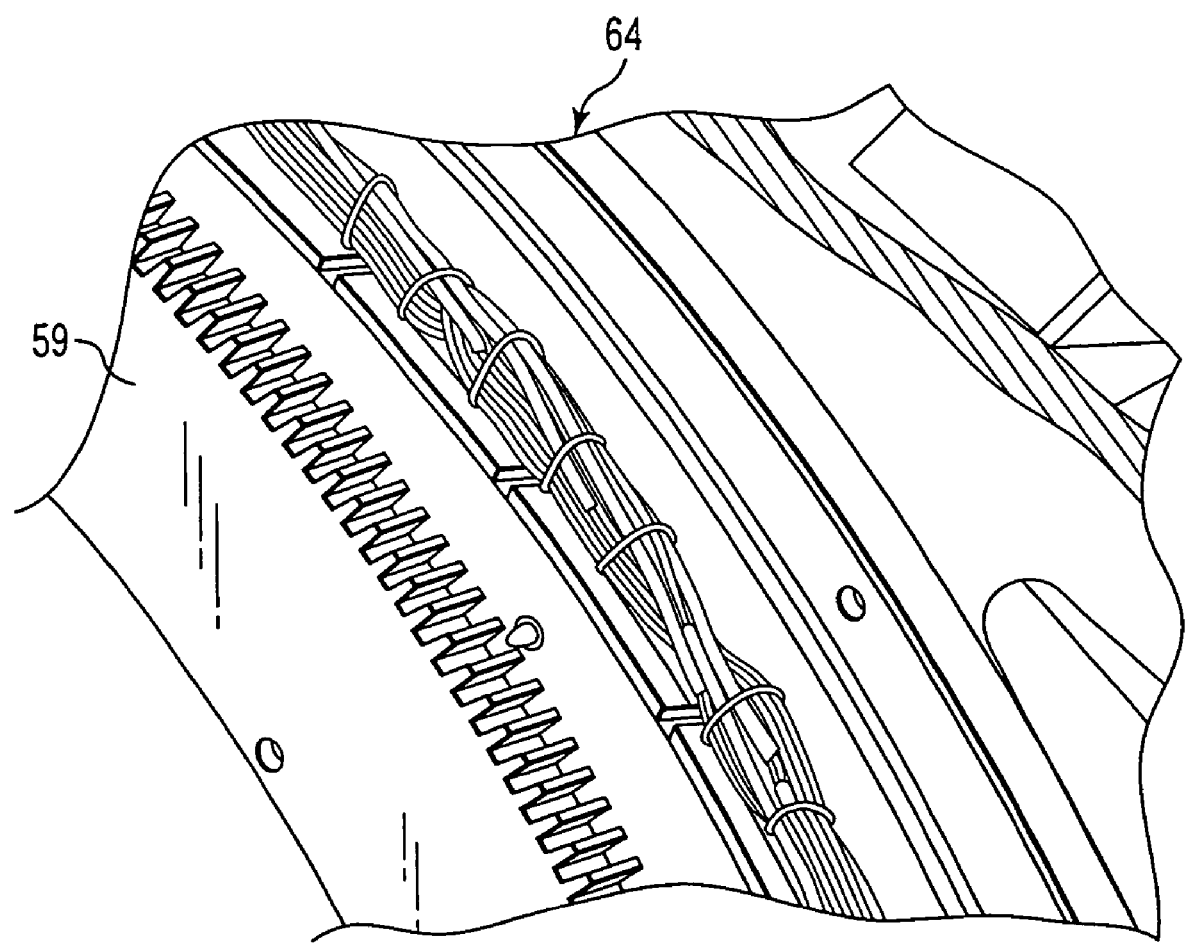
FIG. 12 is a view illustrating a conventional motor comprising a magnet type encoder using a magnetic gear.

According to the first embodiment of the permanent magnet type motor shown in FIGS. 3A and 3B, the weight of a gear 59 used in the conventional structure shown in FIG. 12 can be omitted by using the rotor main body 30 having the land-groove irregular portion formed on the inner periphery face of the rotor main body 30 as the detection target portion 35. In this manner, an inertial moment decreases, and concurrently, the motor capacity or volume can be reduced. Further, an inexpensive and space saving motor can be obtained, reducing the number of parts and reducing a space for a magnet type encoder.

As the modification of the embodiment of FIGS. 3A and 3B, the irregular portion configuring the detection target portion 35 may be formed on the outer periphery face of the rotor main body 30 instead of the inner periphery face of the rotor main body 30. Specifically, a portion may be formed such that the laminate thickness of the rotor main body 30 is increased beneath of a portion at which the permanent magnet 31 of FIG. 3B is provided. In this case, of course, the magnetic sensor 36 also should be moved so as to be opposite to the detection target portion 35.

Figure 4B:
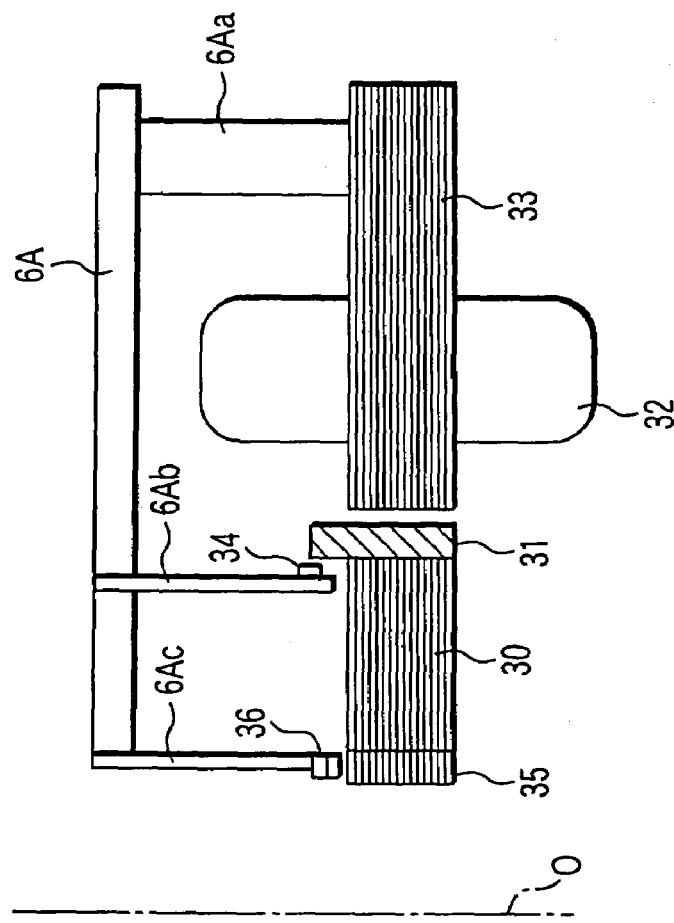
FIGS. 4A and 4B are sectional views in a radial direction and an axial direction, respectively, for illustrating a configuration of a permanent magnet motor according to a second embodiment of the present invention.
Figure 4A:
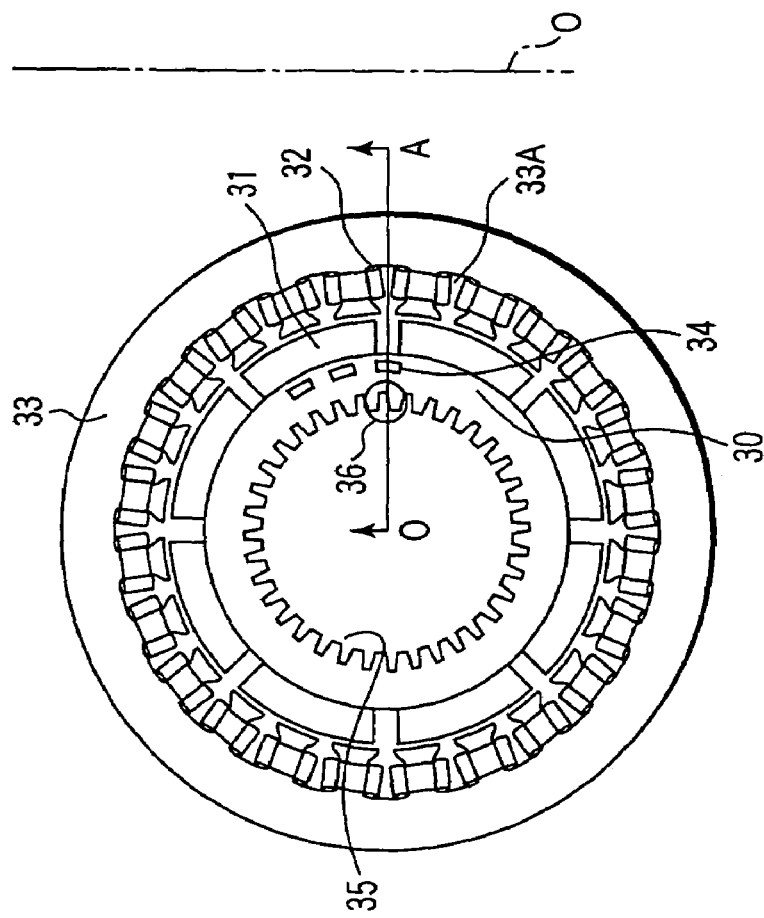

FIG. 4A shows another motor layout view illustrating a second embodiment of a permanent magnet type motor and FIG. 4B shows a sectional view taken along the line O-A of FIG. 4A and seen in a direction indicated by the arrows. A difference from FIGS. 3A and 3B is that a magnetic sensor 36 is provided in a radial direction of the detection target portion 35, so that the detection target portion 35 is at an end face part of a rotator main body 30. The other configuration is identical to that of FIGS. 3A and 3B and a detailed description thereof may be omitted.

Figure 5B:
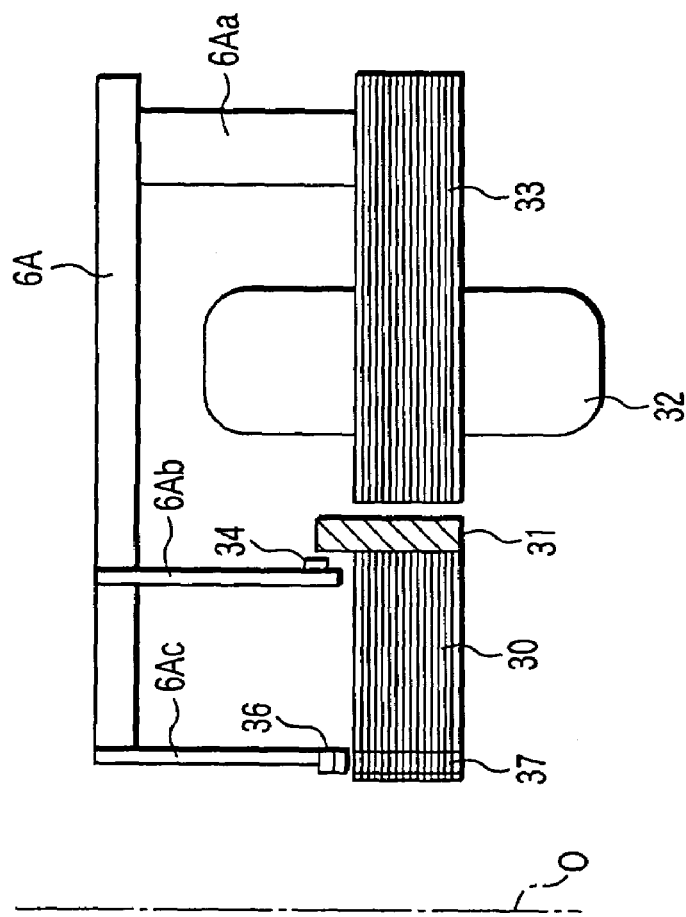
FIGS. 5A and 5B are sectional views in a radial direction and an axial direction, respectively, for illustrating a configuration of a permanent magnet motor according to a third embodiment of the present invention.
Figure 5A:
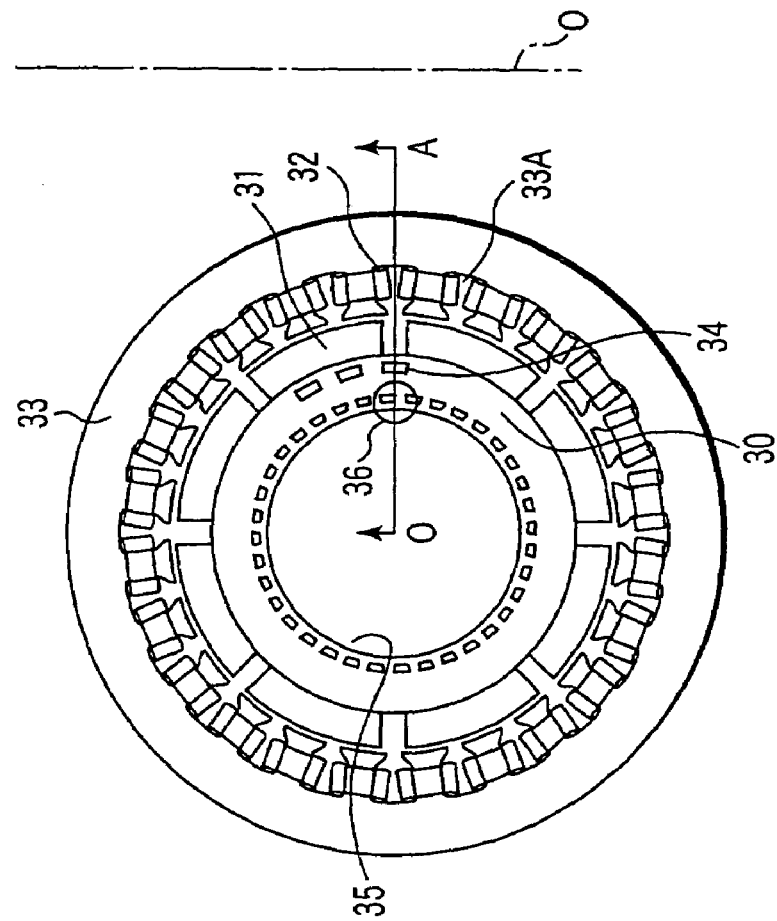

FIG. 5A shows still another motor layout view illustrating a third embodiment of a permanent magnet type motor and FIG. 5B shows a sectional view taken along the line O-A and seen in a direction indicated by the arrows. A difference from FIGS. 4A and 4B is that an irregular portion is not formed as a detection target portion 35 of a rotor main body 30, and instead a plurality of holes 37 are formed periodically (with equal intervals) in a peripheral direction at the inner periphery face side of the rotor main body 30. The other configuration is identical to that of FIGS. 4A and 4B.

Figure 6:
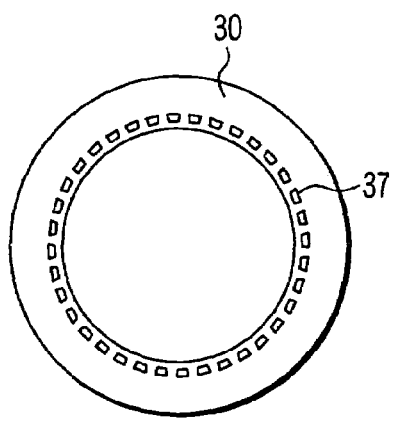
FIG. 6 is a schematic view of a first embodiment motor with a slit plate according to the present invention.
Figure 7:
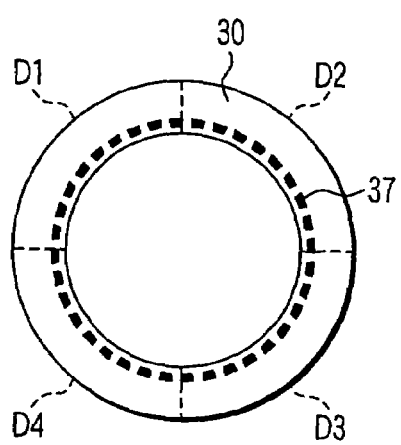
FIG. 7 is a schematic view of a second embodiment motor with a slit plate according to the present invention.

FIGS. 6 and 7 are side views of a rotor main body 30 illustrating a fourth embodiment of the permanent magnet type motor. FIG. 6 shows a press-shaped iron plate 30A a plurality of which are used for configuring the laminated rotor main body 30 shown in FIGS. 3A and 3B. The plate 30A is provided with a plurality of holes 37A to be used as the detection target portion 37.

FIG. 7 is a view of a laminated rotor main body 30 formed by laminating the plate 30A of FIG. 6 in such a manner that when the plates 30A are laminated, edges of the holes 37A of the plates 30A are set out slightly to make a stepwise shape by slightly rotating the plates 30A one by one at an arbitrary angle. In this case, the ring shaped rotor main body 30 may be divided into a plurality of sections (four sections D1 to D4, for example) by dividing the plate 30A along an axial direction at a position of the holes 37A. The other configuration is identical to that of FIGS. 3A and 3B.

In the case where the detection target portion 35 is formed as a land-groove irregular portion according to the embodiments of FIGS. 3A and 4A, the division may be performed at grooves.

Figure 8:
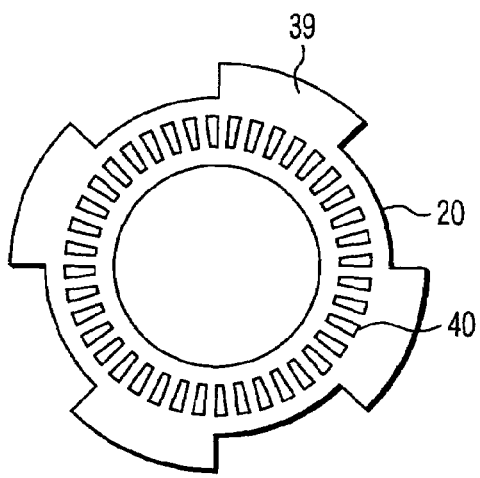
FIG. 8 is a schematic view of a third embodiment motor with a slit plate according to the present invention.

FIGS. 8 and 9 are front views each showing a detection body 20 used in a fifth embodiment of the permanent magnet type motor. These detection target bodies 20 may be mounted directly or via a mount member on one end face in an axial direction of the rotational tubular frame 9B described previously in FIG. 2.

As shown in FIG. 8, the detection body 20 is formed in a substantially ring shape; an irregular portion configuring a magnetic pole position detecting portion 39 at the outer periphery part is formed; and a plurality of slits or rectangle shaped elongated holes 40 configuring a rotational position detecting portion are formed periodically (with equal intervals). Such a detection body 20 may be provided instead of the body 20 having irregular portion which configures the detection target portion 35 of the previously described embodiment such as the embodiment of FIG. 2.

In the detection body 20 having such a configuration as shown in FIG. 8, three optical sensors 41 for detecting a magnetic pole position in proximity to the magnetic pole position detecting portion 39 are arranged along the detection body 20, as shown in FIG. 9. In addition, a magnetic sensor 42 for detecting a rotational position of the rotor main body 30 in proximity to the slit 40 of the detection body 20 is arranged along the detection body 20.

In the case where the detection body 20 is mounted on the rotor main body 30, it is required to mount the magnetic pole position detecting portion 39 at a position synchronized with the previously described permanent magnet 31 shown in FIGS. 3B, 4B and 5B. The optical sensor 41 used here may be of transparent type or may be of reflection type.

Here, in an internal configuration of the magnetic sensor 42, one set of two semiconductor magnetic elements and one magnet are configured, and two semiconductor magnetic elements are disposed in magnetic pole (protrusive pole on which the stator coil 32 is wound) pitches of the rotor main body 30. Thus, with rotation of the rotor main body 30, when its protrusive pole is close to or is distant from the magnetic sensor 42, the magnetic flux passing through the magnetic sensor 42 changes. Then, the electrical resistance of the magnetic sensor 42 changes, whereby a rotational position can be recognized.

According to a fifth embodiment of the permanent magnet type motor described above by referring to FIGS. 8 and 9, the magnetic pole position detecting portion 39 is composed of an irregular portion formed at the outer periphery part of one detection body 20, and the rotational position detecting portion is composed of slits 40. Thus, it is effective to make the entirety of the detection portions compact. In addition, the sensors 41, 42 can be gathered on the detection body 20, and thus, these sensors can be mounted at a position at which maintenance and adjustment are easy, the position being distant from a motor portion. By using the detection body 20, not only the entire weight decreases, but also the inertial moment decreases, and concurrently, the motor weight can be reduced. In addition, the detection body 20 is used, an optical sensor is used for detection of a magnetic pole position, and a magnetic sensor is used for detection of a rotational position. Thus, the interference of detection of both sensors can be prevented.

Figure 10A:
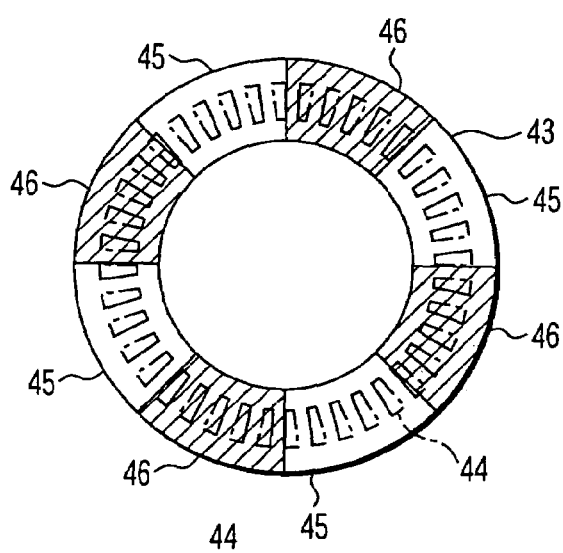
FIGS. 10A and 10B are a plan view and a sectional view, respectively, of a fifth embodiment motor with a slit plate according to the present invention.
Figure 10B:
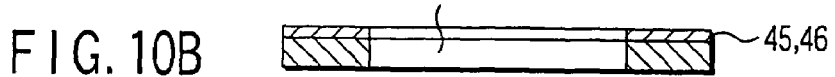

FIGS. 10A and 10B are a front view and a sectional view each showing a detection body 43 illustrating a sixth embodiment of the permanent magnet type motor. This detection body 43 is mounted directly or via a mount member on the rotational tubular frame 9 as shown in FIG. 2 or on an end face of the rotor main body 30 in an axial direction of the rotor main body 30, as in FIGS. 8 and 9, and a plurality of slits 44 which are arranged in a circular ring shape are formed periodically (with equal intervals) at the internal part of the detection body 43.

Along the side surface of the detection body 43, pairs of non-magnetic members are arranged with equal intervals at positions corresponding to the slits 44. Pairs of members having different reflection index for detecting a magnetic pole position, are disposed. As a non-magnetic member pair, for example, white and black tapes 45, 46 are used. These white and black tapes 45, 46 are applied to a full face of the body 43 including a portion at which the slits 44 of the detection body 43 are formed.

An optical sensor is arranged in proximity to the slits 44 of the detection body 43. The optical sensor is provided for detecting a rotational position of the rotor main body 30. Specifically, a reflection type optical sensor is used in this case. Further, a sensor is positioned in proximity to the non-magnetic members 45, 46 of the detection body 43 for detecting a magnetic pole position of the permanent magnet of the rotor main body 30.

Such a detection body 43 is provided instead of the land-groove irregular portion configuring the detection target portion 35 according to the previously described embodiments. A configuration other than the above-described configuration is similar to those of another embodiments.

According to the sixth embodiment of the above-described permanent magnet type motor, a simple configuration is provided as compared with that of the fifth embodiment. This configuration can be used for a motor of a large diameter. In this case, a detection body 43 having a divided configuration may be used.

Modifications

While the previously described embodiments of the motor shown in FIGS. 8 and 9 have been explained with respect to an X-ray CT apparatus, any motor according to the other embodiments may be applied to the previously described X-ray CT apparatus.

The previously described embodiments have been described to have an inner rotor type motor of which a stator has been disposed at the outer periphery side of the rotor. Instead, an outer rotor type motor of which the stator has been disposed at the inner periphery side of the rotor can be carried out similarly.

Further, as the magnetic resistance change portion of the previously described detection target portion 35, a description has been given with respect to an example in which a land-groove irregular portion is periodically formed on the inner periphery face of the rotor main body (rotor yoke) 30. However, this irregular portion may be periodically formed on the outer periphery face or side face of the rotor main body 30.

In addition, as the magnetic resistance change portion of the previously described detection target portion, a description has been given with respect to an example in which a plurality of holes are periodically formed in the inner periphery side of the rotor main body 30. However, the plurality of holes may be periodically formed on the outer periphery face or side face of the rotor main body 30.

While the previously described embodiments each has been provided as a laminated body in which the rotor main body 30 has a silicon steel plate or an iron plate laminated in number, this body may be formed in a cylindrical shape body by means of a solid magnetic body, and a gear for configuring a detection body may be formed on the outer periphery face or inner periphery face of the solid body.

According to the present invention described above, there can be provided a permanent magnet type motor capable of reducing the number of parts; capable of using a magnet type encoder with an simple configuration in a large diameter motor of a hollow shaft type; and capable of being mounted at a position at which maintenance and adjustment are easy, the position being distant from the motor portion. In addition, there can be provided an X-ray CT apparatus capable of making the entirety compact, the X-ray CT apparatus being capable of achieving cost reduction.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A permanent magnet type motor comprising:
    a ring shaped rotor main body which is rotatably supported with respect to a stationary member;
    a rotor which is provided on an outer periphery face of the rotor main body and which is arranged such that S poles and N poles of a plurality of permanent magnets are provided alternately;
    a stator composed of a stator core arranged at the outer periphery side or inner periphery side of the rotor, the stator core having winding storage portions, and stator windings stored in the winding storage portions;
    a detection target body mounted directly or via a mount member on an end face in an axial direction of the rotor main body, the detection target body having a magnetic pole position detecting portion and a rotational position detecting portion;
    a first sensor arranged in proximity to the magnetic pole position detecting portion of the detection target body, the first sensor detecting a magnetic pole position; and
    a second sensor arranged in proximity to the magnetic pole position detecting portion of the detection target body, the second sensor detecting a rotational position of the rotor main body, wherein the magnetic pole position detecting portion of the detection target body includes an irregular portion formed on an outer periphery edge thereof, and the rotational position detecting portion includes a plurality of slits or a plurality of holes periodically formed along a circle drawn at an inner part of the detection target body concentrically.

2. A permanent magnet type motor according to claim 1, wherein the first sensor which detects a magnetic pole position is an optical sensor, and the second sensor which detects a rotational position of the rotor main body is a magnetic sensor.

3. A permanent magnet type motor according to claim 1, wherein the irregular portion is formed on the detection target body periodically as a magnetic resistance change portion.

4. A permanent magnet type motor according to claim 3, wherein the irregular portion is formed as a gear made of a magnetic material.

5. A permanent magnet type motor according to claim 1, wherein the irregular portion includes a plurality of holes periodically formed on the detection target body.

6. A permanent magnet type motor according to claim 1, wherein the rotor main body is configured by laminating iron plates or silicon steel plates or composed of a solid magnetic body.

7. A permanent magnet type motor according to claim 1, wherein the rotor main body is fixed at an inner periphery of a movable part of a bearing so that the rotor main body is rotatably supported on the stationary member.

8. A permanent magnet type motor according to claim 7, wherein the stationary member is configured as a stationary tubular frame having a cross section formed in a substantially tapered shape with respect to a tube axis, and a fixing part of the bearing is mounted at an end of a small diameter portion of the stationary tubular frame.

9. A permanent magnet type motor comprising:
a ring-shaped rotor main body which is rotatably supported with respect to a stationary member;
a rotor which is provided on an outer periphery face of the rotor main body and which is arranged such that S poles and N poles of a plurality of permanent magnets are provided alternately;
a stator composed of a stator core arranged at the outer periphery side or inner periphery side of the rotor, the stator core having winding storage portions, and stator windings stored in the winding storage portions;
a detection target body mounted directly or via a mount member on an end face in an axial direction of the rotor main body, the detection target body having a magnetic pole position detecting portion and a rotational position detecting portion;
a first sensor arranged in proximity to the magnetic pole position detecting portion of the detection target body, the first sensor detecting a magnetic pole position; and
a second sensor arranged in proximity to the magnetic pole position detecting portion of the detection target body, the second sensor detecting a rotational position of the rotor main body,
wherein the rotational position detecting portion of the detection target body includes a plurality of slits or a plurality of holes periodically formed along a circle drawn at an inner part of the detection target body concentrically, and the magnetic pole position detecting portion of the detection target body includes at least a pair of non-magnetic members disposed and fixed so as to shield the plurality of slits or the plurality of holes of the rotational position detecting portion, the non-magnetic members having different light reflection indexes.

10. A permanent magnet type motor according to claim 9, wherein the first sensor which detects a magnetic pole position is an optical sensor, and the second sensor which detects a rotational position of the rotor main body is a magnetic sensor.

11. A permanent magnet type motor according to claim 9, wherein the rotor main body is configured by laminating iron plates or silicon steel plates or composed of a solid magnet body.

12. A permanent magnet type motor according to claim 9, wherein the rotor main body is fixed at an inner periphery of a movable part of a bearing so that the rotor main body is rotatably supported on the stationary member.

13. A permanent magnet type motor according to claim 12, wherein the stationary member is configured as a stationary tubular frame having a cross section formed in a substantially tapered shape with respect to a tube axis, and a fixing part of the bearing is mounted at an end of a small diameter portion of the stationary tubular frame.

* * * * *